United States Patent
Müller et al.

(10) Patent No.: US 6,194,600 B1
(45) Date of Patent: Feb. 27, 2001

(54) METHOD OF PRODUCING AMINOCYANOACETAMIDE

(75) Inventors: Hans Rudolf Müller, Schaffhausen; Heinrich Bollinger, Beringen; Peter Schwaninger; Martin Kurz, both of Schaffhausen, all of (CH)

(73) Assignee: Eprova A.G., Schaufthausen (CH)

( * ) Notice: Subject to any disclaimer, the term of this patent is extended or adjusted under 35 U.S.C. 154(b) by 0 days.

(21) Appl. No.: 09/475,265

(22) Filed: Aug. 26, 1999

Related U.S. Application Data

(63) Continuation-in-part of application No. 09/215,347, filed on Dec. 18, 1998, now abandoned.

(30) Foreign Application Priority Data

Dec. 18, 1997 (CH) .................................................... 2907/97

(51) Int. Cl.[7] .................................................. C07C 255/00
(52) U.S. Cl. ............................................................ 558/455
(58) Field of Search ............................................... 558/445

(56) References Cited

FOREIGN PATENT DOCUMENTS 0 342 616   11/1989   (EP) .

OTHER PUBLICATIONS

Smith, Jr. et al., Journal of the American Chemical Society, vol. 76, No. 23, (1954), pp. 6080–6084.

*Primary Examiner*—Joseph K. McKane
*Assistant Examiner*—Joseph Murray
(74) *Attorney, Agent, or Firm*—Millen, White, Zrlano & Branigan, P.C.

(57) ABSTRACT

With the present method, a process which can be employed industrially can be used for the first time for the direct production of aminocyanoacetamide. The method is based on the reaction of cyanoacetamide with nitrites to form nitrosocyanoacetamide at a pH of around 2 and on the subsequent catalytic hydrogenation of nitrosocyanoacetamide to form aminocyanoacetamide.

21 Claims, No Drawings

METHOD OF PRODUCING AMINOCYANOACETAMIDE

CROSS-REFERENCE TO RELATED APPLICATION

This application is a continuation-in-part of application Ser. No. 09/215,347 filed Dec. 18, 1998, now abandoned claiming priority of Swiss application number 2907/97 filed Dec. 18, 1997.

FIELD OF THE INVENTION

This invention relates to a new method of producing aminocyanoacetamide which can be employed industrially. Aminocyanoacetamide is an intermediate which is of interest for the production of imidazoles, pyrazines, purines or pteridines for example.

BACKGROUND OF THE INVENTION

Various methods of producing aminocyanoacetamide are known. Those which should be mentioned in particular are that of Smith Jr. et al., who in *J. Am. Chem. Soc.,* 76, 6080 (1954) describe a method of producing aminocyanoacetamide from hydroxyiminocyanoacetamide by hydrogenation with aluminium amalgam, and various methods of producing aminocyanoacetamide from esters of cyanoacetic acid via esters of aminocyanoacetic acid such as that according to EP 0 342 616, which discloses the production of aminocyanoacetamide by the nitrosylation of an ester or cyanoacetic acid by means of an alkali nitrite, hydrogenation of the resulting ester of hydroxyiminocyanoacetic acid with platinum/hydrogen and the subsequent liberation of aminocyanoacetamide with aqueous ammonia. The method of Smith Jr. et al. cannot be employed industrially due to the problems of using a mercury catalyst. Methods of producing aminocaynoacetamide from esters of cyanoacetic acid via esters of aminocyanoacetic acid such as that described in EP 0 342 616 are methods which are costly on an industrial scale and which are based on the cumbersome reaction of cyanoacetic acid which is protected by an ester function to form an ester of aminocyanoacetic and the subsequent liberation of aminocyanoacetamide.

SUMMARY OF THE INVENTION

With the present method, a process which can be employed industrially can be used for the first time for the direct production of aminocyanoacetamide. The method is based on the reaction of cyanoacetamide with nitrites at a pH below 2.6 and of preferably around 2 to form nitrosocyanoacetamide and the subsequent catalytic hydrogenation of nitrosocyanoacetamide to form aminocyanoacetamide. By "around 2" is meant 1.5–2.5 and narrower ranges, e.g. 1.6–2.4 or 1.8–2.2.

Cyanoacetamide is a starting material which is commercially available on large scale. Cyanoacetamide is nitrosylated with nitrites at a pH of preferably around 2 to form nitrosocyanoacetamide. An alkali nitrite is preferably used for nitrosylation, and is preferably added to an acidic solution or suspension of cyanoacetamide. The pH is preferably held at around 2 during nitrosylation. This procedure prevents the formation of very large amounts of by-products, reduces the amount of nitrous gases which are formed and yields a product which can readily be centrifuged.

The customary nitrites for nitrosylation are alkali nitrites, preferably sodium nitrite. The nitrite is used in an amount of 1–5 equivalents with respect to cyanoacetamide, preferably 1–2 equivalents with respect to cyanoacetamide. Nitrosylation is conducted in acidic media, preferably in strong, concentrated mineral acids, and in particular is preferably conducted in hydrochloric acid at a pH of around 2. The reaction takes placed in a concentrated solution or preferably in a suspension, at temperatures between 0° C. and 50° C., preferably between 0° C. and 5° C. In particular, a pH of preferably around 2 within this reaction step results in a direct crystallization of nitrosocyanoacetamide. At higher pH values, namely above 2.6, which is the pH of an aqueous solution of nitrosocyanoacetamide, the undesired semi-sodium salt precipitates. This undesired semi-sodium salt is obtained in a very fine form and therefore on an industrial scale the product is hardly separable and washable. Such a product will always also contain high amounts of sodium chloride and by-products of the reaction. Another drawback of the precipitation of the semi-sodium salt is that it is a highly exothermal reaction forcing the hydrolysis of cyanoacetamide. Thus, the reaction is conducted at a pH lower than 2.6 under conditions wherein essentially no undesired semi-alkali metal (especially sodium) salt precipitates.

The nitrosocyanoacetamide which is thus obtained is reacted by catalytic hydrogenation to form aminocyanoacetamide. Hydrogenation is effected with hydrogen in the presence of a catalyst. Suitable catalysts are preferably noble metal catalysts such as platinum, which is finely divided in amounts of 1% to 20% on conventional support materials such as carbon, alumina, silica, barium sulphate or calcium carbonate, or platinum oxide. Platinum in an amount of 2% to 10% on carbon is preferably used as the catalyst.

The catalyst is advantageously used in amounts of 1% to 30% with respect to the nitrosocyanoacetamide, most preferably 2% to 10% with respect to the nitrosocyanoacetamide.

Hydrogenation is conducted either in aqueous media such as water, or is preferably conducted in what are predominantly nonaqueous media, e.g. in low molecular weight, water-miscible alcohols such as methanol or ethanol, in low molecular weight, water-miscible carboxylic acids such as formic acid or acetic acid, or in tetrahydrofuran. A little sodium hydrogen phthalate can be added to buffer aqueous hydrogenation solutions. Other additives can be added to the hydrogenation solution, such as iron sulphate to prevent the formation of gaseous hydrogen cyanide, Raney nickel to prevent poisoning of the catalyst, etc.

Even when working in nonaqueous media, the use of hydrous catalysts does not give rise to problems. After the reaction is complete, the catalysts used can easily be worked up again and used for the next reactions.

Hydrogenation is effected at a pressure of 1 bar to 100 bar, preferably 1 bar to 10 bar, and at temperatures between 0° C. and 80° C., preferably between 20° C. and 50° C. The time of hydrogenation can vary between 30 minutes and 20 hours depending on the pressure, temperature, medium and amount of catalyst.

After the completion of hydrogenation in aqueous media the pH of the reaction solution can be lowered by the addition of an acid such as acetic acid. This procedure prevents the formation of very large amounts of by-products.

Another aspect of the invention is the single step process of producing nitrosocyanoacetamide from cyanoacetamide and the resultant compound.

Still another aspect is the single step of hydrogenation of the nitrosocyanoacetamide to aminocyanoacetamide.

In the foregoing and in the following examples, all temperatures are set forth uncorrected in degrees Celsius and unless otherwise indicated, all parts and percentages are by weight.

The entire disclosures of all applications, patents and publications, cited above, and of Swiss Application No. 2907/97, filed Dec. 18, 1997, are hereby incorporated by reference.

EXAMPLES TO ILLUSTRATE THE INVENTION

Example 1
Production of nitrosocyanoacetamide 33.5 kg cyanoacetamide were placed in 78 l water in a reaction vessel and adjusted to pH 2.3 with 0.1 kg of 37% hydrochloric acid. A solution of 28.7 kg sodium nitrite in 45 l water was then added over 7 hours. In the course of the addition, the pH of the reaction solution was held between 1.5 and 2.5 by adding a total of 36 kg of 37% hydrochloric acid. The temperature of the reaction solution was maintained below 40° C. Nitrosocyanoacetamide crystallised from the clear yellowish-red solution which was formed during the addition of the sodium nitrite solution, even before the addition was complete. The yellow suspension was stirred overnight at room temperature and was subsequently cooled to 5° C.

The thick, white crystallisation slurry which was thus obtained was centrifuged off at 5° C., and was subsequently washed with water and dried at 50° C. under vacuum. 33.9 kg nitrosocyanoacetamide were obtained, with a content of 99.1% as determined by titration. The substance was identified by means of IR and NMR measurements. Comparison of these spectra with those of a reference substance showed that the values were identical.

Example 2
Production of nitrosocyanoacetamide 250 ml 37% hydrochloric acid (3 moles) were placed in a reaction vessel at 0° C. and were treated with 171.6 g cyanoacetamide (2 moles). A solution of 156.0 g sodium nitrite (2.26 moles) in 600 ml water was added drop-wise thereto, with stirring, over 5–7 hours. The temperature was maintained at 0° C. to 3° C. during the addition. The resulting white crystalline product was filtered off under suction, and was subsequently washed with water and dried at 40° C. under vacuum. 142.6 g nitrosocyanoacetamide was obtained, with a content of 97.4% as determined by means of HPLC. The proportion of cyanoacetamide in the product thus obtained was 0.3%, as determined by means of HPLC.

Example 3
Production of nitrosocyanoacetamide 2.0 kg cyanoacetamide and 1.8 kg sodium nitrite were placed in 4.3 l water. After heating to 20° C., 2.4 l 37% hydrochloric acid were added drop-wise over 6 hours. The temperature was maintained at 40° C. to 50° C. during the addition. After the addition was complete, the resulting suspension was stirred for a further 40–50 minutes at 35° C. to 40° C. and was thereafter cooled to 10° C.

The resulting white crystalline product was filtered off under suction, and was subsequently washed with water and dried at 40° C. under vacuum. 2.5 kg nitrosocyanoacetamide was obtained, with a content of 90.7%.

The 2.5 kg nitrosocyanoacetamide which were thus obtained were heated to boiling in 7.1 l isopropanol and were treated with 70 ml water. After 2 hours the suspension was filtered to clarify it. The residue was washed with 800 ml of hot isopropanol. After concentrating the filtrates to about 4 l, the yellowish suspension was maintained at −20° C. overnight.

The resulting white crystalline product was filtered off under suction, and was subsequently washed with water and dried at 40° C. under vacuum. 2.0 kg nitrosocyanoacetamide was obtained, which had a content of 100.0% and a decomposition point of about 170° C. The proportion of NaCl in the product thus obtained was less than 0.5%.

Example 4
Production of nitrosocyanoacetamide 7.5 l of 37% hydrochloric acid were placed in a vessel and treated with 5.15 kg cyanoacetamide. A solution of 4.68 kg sodium nitrite in 1.8 l water was added drop-wise thereto, with stirring, over 3 hours. The temperature was maintained at 5° C. during this addition.

The resulting white crystalline product was filtered off under suction, and was subsequently washed with water and dried at 40° C. under vacuum. 5.47 kg nitrosocyanoacetamide were obtained, which had a content of 98.7% as determined by means of HPLC. The chloride content of the product thus obtained was 0.4%.

Example 5
Production of aminocyanoacetamide 31 g nitrosocyanoacetamide (0.27 moles) were placed in 700 ml methanol in a steel autoclave and were treated with 20 g of a platinum catalyst (5% on carbon with 50% water). After flushing with nitrogen and hydrogen the batch was hydrogenated at room temperature and 2 bar hydrogen pressure for 14 hours.

After depressurisation, the autoclave contents were filtered under suction and the light yellow filtrate obtained was concentrated under vacuum until crystallisation occurred. The crystalline product was slurried in 250 ml isopropanol, filtered under suction and at dried at 40° C. under vacuum. 23 g aminocyanoacetamide were obtained, which was slightly light beige in colour and had a content of 84.1% as determined by means of HPLC and a decomposition point of about 120° C.

Example 6
Production of aminocyanoacetamide

Hydrogenations were performed, analogously to example 5, in the following media and with the catalysts listed.

| Solvent | Amount of catalyst | Pt content | Temperature | Duration of hydrogenation | Yield | Content |
|---|---|---|---|---|---|---|
| a tetrahydrofuran | 5 g | 5.0% | RT | 27 hrs | 52.7% | 88.0% |
| b ethanol | 5 g | 5.0% | RT | 50 hrs | 79.2% | 79.1% |
| c methanol | 20 g | 2.5% | RT | 17 hrs | 87.1% | 80.8% |
| d 40% acetic acid | 7.75 g | 5.0% | 25° C. | 10 hrs | 66.2% | 94.2% |
| e 40% acetic acid | 7.75 g | 5.0% | 24° C. | 8 hrs | 69.4% | 97.5% |
| f 40% acetic acid | 7.75 g | 5.0% | 25° C. | 7 hrs | 72.6% | 99.2% |
| g water | 7.75 g | 5.0% | 24° C. | 6 hrs | 66.5% | 89.6% |
| h 0.25% acetic acid | 7.75 g | 5.0% | 24° C. | 5 hrs | 75.7% | 97.0% |
| i water | 7.75 g | 5.0% | 24° C. | 6 hrs | 68.1% | 98.9% |
| j water | 7.75 g | 5.0% | 10° C. | 9 hrs | 73.8% | 99.9% |
| k water | 7.75 g | 5.0% | 12° C. | 9 hrs | 69.0% | 99.9% |
| l water | 7.75 g | 5.0% | 11° C. | 8 hrs | 72.1% | 99.5% |
| m water | 7.75 g | 5.0% | 12° C. | 17 hrs | 81.4% | 96.0% |
| n water | 7.75 g | 5.0% | 12° C. | 20 hrs | 77.8% | 88.8% |
| o water | 7.75 g$^1$ | 5.0% | 23° C. | 9 hrs | 74.4% | 85.6% |
| p water | 7.75 g$^1$ | 5.0% | 23° C. | 7 hrs | 78.5% | 99.5% |
| q water | 7.75 g$^1$ | 5.0% | 23° C. | 7 hrs | 80.1% | 99.9% |
| r water | 7.75 g$^1$ | 5.0% | 23° C. | 7 hrs | 83.0% | 99.9% |

-continued

| Solvent | Amount of catalyst | Pt content | Temperature | Duration of hydrogenation | Yield | Content |
|---|---|---|---|---|---|---|
| s water | 7.75 g[1] | 5.0% | 23° C. | 7 hrs | 81.9% | 99.9% |
| t water | 7.75 g[1] | 5.0% | 23° C. | 7 hrs | 82.6% | 99.9% |

[1] The catalyst used in the preceding batch in each case was used in examples o to t. The catalyst was worked up each time by washing with water/dilute hydrochloric acid and subsequent drying at 130° C.

Example 7
Production of aminocyanoacetamide 200 g nitrosocyanoacetamide (1.77 moles) were placed in 2 l water in a steel autoclave and treated with 49.45 g of a platinum catalyst (5% on carbon). After flushing with nitrogen and hydrogen, the batch was hydrogenated at 24° C. and 2 bar hydrogen pressure for 8 hours.

After depressurisation, 117 ml acetic acid was added to the hydrogenation solution. The clarified, filtered yellowish hydrogenation solution was concentrated under vacuum at 50° C. until crystallisation occurred. The crystalline product was treated with 450 ml isopropanol and maintained at 0° C. overnight.

The resulting crystalline product was filtered under suction, and was subsequently washed with cold isopropanol and dried at 40° C. under vacuum. 136.7 g of very slightly light yellowish aminocyanoacetamide were obtained, with a content of 99.7% as determined by means of titration and a content of aminomalonic acid diamide of 0.26% as determined by means of HPLC.

100 g of the crude aminocyanoacetamide which was thus obtained were dissolved in 240 ml water at 85° C. and rapidly cooled to 0° C. The crystalline product which was thus obtained was filtered under suction, and was subsequently washed with cold isopropanol and dried at 40° C. under vacuum. 79.2 g of colourless aminocyanoacetamide was obtained, which had a content of 100.0% as determined by means of HPLC.

Similarly, 20 g of the crude aminocyanoacetamide obtained were dissolved in a mixture of 200 ml water and 600 ml isopropanol at 20° C. and rapidly cooled to 0° C. The crystalline product thus obtained was filtered off under suction, and was subsequently washed with a cold mixture of water and isopropanol and was dried at 40° C. under vacuum. 11.6 g of colourless aminocyanoacetamide was obtained, with a content of 100.0% as determined by means of HPLC.

At room temperature, the product which was thus obtained exhibited a solubility in methanol of 1.65 g/100 ml and a solubility in ethanol of 0.85 g/100 ml.

Example 8
Production of aminocyanoacetamide 8.5 kg of a platinum catalyst (5% on carbon with about 50% water) were placed in a hydrogenation reactor which had been rendered inert and were treated with 119 kg methanol. 14.7 kg nitrosocyanoacetamide (130 moles) were added to this suspension. After flushing with nitrogen and hydrogen, the batch was hydrogenated at 40–45° C. and 2 bar hydrogen pressure for 11 hours.

After depressurisation, the hydrogenation solution was clarified by filtration and the filtrate was cooled to −18° C. overnight The resulting crystalline product was centrifuged off, and was subsequently washed with cold ethanol and dried at 40° C. under vacuum. 8.3 kg of slightly yellowish aminocyanoacetamide was obtained, with a content of 99.2% as determined by means of HPLC and a content of nitrosocyanoacetamide of 3.5% as determined by means of HPLC.

By recrystallisation in an analogous manner to example 7, colourless amino cyanoacetamide was obtained, with a content of 100.0% as determined by means of HPLC and a content of nitrosocyanoacetamide of <0.1% as determined by means of HPLC.

In the preceding examples, the calculated yields in % of theory without respecting the purity are:

| Example 1 | 33.9 kg | (75.2%) |
| Example 2 | 142.6 kg | (61.8%) |
| Example 3 | 2.5 kg | (93.0%) |
| Example 4 | 5.47 kg | (79.0%) |
| Example 5 | 23 g | (84.7%) |
| Example 7 | 136.7 g | (78.0%) |
| Example 8 | 8.3 kg | (64.4%) |

Comparative Experiments of the Hydrogenation Step

If instead of the use of catalytic hydrogenation, Raney nickel is employed, remarkably poorer results are obtained, as seen from the following table:

| Ratio nitrosocyanoacetamide to Raney nickel | Temperature | Consumption of hydrogen | Purity of aminocyanoacetamide [1] | Remaining content of nitrosocyano acetamide [1] |
|---|---|---|---|---|
| 1:1 | 40° C. | 6 equivalents | * | * |
| 1:0.33 | 20° C. | 2 equivalents | 4.4% | 72.1% |
| 1:0.15 | 20° C. | 3 equivalents | 4.0% | 53.6% |

* not measured
[1] measured by HPLC

The preceding examples 1–8 can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of producing aminocyanoacetamide, comprising reacting cyanoacetamide with an alkali metal nitrite, at a pH of less than 2.6 and under conditions wherein little or no semi-alkali metal salt precipitates, to form nitrosocyanoacetamide and subjecting the latter to catalytic hydrogenation to form aminocyanoacetamide.

2. A method according to claim 1, wherein the cyanoacetamide is placed in a hydrochloric acid medium and the nitrite is added thereto in order to form the nitrosocyanoacetamide.

3. A method according to claim 1, wherein the pH is held constant at about 2 during the nitrosylation of cyanoacetamide to form nitrosocyanoacetamide.

4. A method according to claim 1, wherein the nitrite is a sodium nitrite.

5. A method according to claim 1, wherein the nitrite is used in an amount of 1–5 equivalents with respect to the cyanoacetamide.

6. A method according to claim 1, wherein the cyanoacetamide is reacted with a nitrite to form nitrosocyanoacetamide in a suspension.

7. A method according to claim 1, wherein cyanoacetamide is reacted with a nitrite to form nitrosocyanoacetamide at temperatures between 0° C. and 50° C.

8. A method according to claim 1, wherein the nitrosocyanoacetamide is reacted to form aminocyanoacetamide by catalytic hydrogenation in an aqueous media.

9. A method to claim 1, wherein the nitrosocyanoacetamide is reacted to form aminocaynoacetamide by catalytic hydrogenation in a nonaqueous media selected from the group consisting of, a water-miscible alcohol, a water-miscible carboxylic acid and tetrahydrofuran.

10. A method according to claim 9, wherein the nitrosocyanoacetamide is reacted to form aminocyanoacetamide by catalytic hydrogenation in methanol.

11. A method according to claim 1, wherein the catalyst for hydrogenation is platinum oxide or a finely divided noble metal catalyst in amounts of 1% to 20% by weight on a support selected from the group consisting of carbon, alumina, silica, barium sulphate and calcium carbonate.

12. A method according to claim 1, wherein the catalyst for hydrogenation is platinum in an amount of 2% to 10% by weight on carbon.

13. A method according to claim 11, wherein in the catalytic hydrogenation of nitrosocyanoacetamide to form aminocyanoacetamide, the catalyst is used in amounts of 1% to 30% with respect to nitrosocyanoacetamide.

14. A method according to claim 1, wherein nitrosocyanoacetamide is reacted to form aminocyanoacetamide by catalytic hydrogenation with hydrogen at 1 bar to 100 bar, and at temperatures between 0° C. and 80° C.

15. A method according to claim 5 wherein the amount of nitrite used 1–2 equivalents with respect to cyanoacetamide.

16. A method according to claim 7 wherein the temperature is between 0° and 5° C.

17. A method according to claim 14 wherein the pressure is 1 bar to 10 bar and the temperature is between 20° C. and 50° C.

18. A method of preparing aminocyanoacetamide comprising catalytically hydrogenating nitrosocyanoacetamide.

19. A method of preparing nitrosocyanoacetamide comprising reacting an alkali metal nitrite with cyanoacetamide at a pH below 2.6 under conditions wherein little or no semi-alkali metal salt precipitates.

20. A method according to claim 19, wherein the pH is around 2.

21. A method according to claim 20, wherein the nitrite is sodium nitrite and the cyanoacetamide is placed in an aqueous solution of hydrochloric acid.

* * * * *